US009642895B2

(12) United States Patent
Dai et al.

(10) Patent No.: US 9,642,895 B2
(45) Date of Patent: May 9, 2017

(54) PEPTIDES FOR ENHANCING TRANSDERMAL DELIVERY

(71) Applicant: 3M INNOVATIVE PROPERTIES COMPANY, Saint Paul, MN (US)

(72) Inventors: Minghua Dai, Plymouth, MN (US); Dmitri V. Smirnov, Plymouth, MN (US); Paul D. Wightman, Louisville, KY (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 14/911,019

(22) PCT Filed: Aug. 12, 2014

(86) PCT No.: PCT/US2014/050683
§ 371 (c)(1),
(2) Date: Feb. 8, 2016

(87) PCT Pub. No.: WO2015/023649
PCT Pub. Date: Feb. 19, 2015

(65) Prior Publication Data
US 2016/0199498 A1 Jul. 14, 2016

Related U.S. Application Data

(60) Provisional application No. 61/864,964, filed on Aug. 12, 2013.

(51) Int. Cl.
A61K 38/00 (2006.01)
A61K 38/28 (2006.01)
A61K 9/00 (2006.01)
A61K 39/00 (2006.01)
A61K 45/06 (2006.01)
A61L 27/22 (2006.01)
A61K 38/09 (2006.01)
C07K 7/06 (2006.01)
A61K 31/575 (2006.01)
A61K 47/42 (2017.01)
A61K 8/64 (2006.01)
A61Q 19/00 (2006.01)
A61Q 19/08 (2006.01)
A61K 39/39 (2006.01)

(52) U.S. Cl.
CPC ............ A61K 38/28 (2013.01); A61K 8/64 (2013.01); A61K 9/0014 (2013.01); A61K 31/575 (2013.01); A61K 38/09 (2013.01); A61K 39/0005 (2013.01); A61K 39/39 (2013.01); A61K 45/06 (2013.01); A61K 47/42 (2013.01); A61L 27/227 (2013.01); A61Q 19/00 (2013.01); A61Q 19/001 (2013.01); A61Q 19/08 (2013.01); C07K 7/06 (2013.01); A61K 38/00 (2013.01); A61K 2039/54 (2013.01); A61K 2039/55516 (2013.01); A61K 2039/60 (2013.01)

(58) Field of Classification Search
None
See application file for complete search history.

(56) References Cited

U.S. PATENT DOCUMENTS

| 4,472,480 | A | 9/1984 | Olson |
| 4,751,087 | A | 6/1988 | Wick |
| 4,834,979 | A | 5/1989 | Gale |
| 5,688,523 | A | 11/1997 | Garbe |
| 6,004,578 | A | 12/1999 | Lee |
| 6,024,976 | A | 2/2000 | Miranda |
| 6,149,935 | A | 11/2000 | Chiang |
| 6,365,178 | B1 | 4/2002 | Venkateshwaran |
| 7,659,252 | B2 | 2/2010 | Wen |
| 2003/0054025 | A1 | 3/2003 | Cantor |
| 2004/0049150 | A1 | 3/2004 | Dalton |
| 2004/0202708 | A1 | 10/2004 | Roehrig |
| 2007/0060512 | A1 | 3/2007 | Sadeghi |
| 2012/0128756 | A1 | 5/2012 | Hsu |
| 2013/0108662 | A1 | 5/2013 | Brock |

FOREIGN PATENT DOCUMENTS

| WO | WO 02/24225 | 3/2002 |
| WO | WO 2004/020405 | 3/2004 |
| WO | WO 2007/076904 | 7/2007 |
| WO | WO 2011/066493 | 6/2011 |
| WO | WO 2012/064429 | 5/2012 |
| WO | WO 2012/167081 | 12/2012 |
| WO | WO 2013/112488 | 8/2013 |

OTHER PUBLICATIONS

Berge et al. 1977. *J. Pharm. Sci.* 66:1-19. "Pharmaceutical Salts".
Chen et al. 2006. *Nature Biotechnology*. 24(4):455-460. "Transdermal protein delivery by a coadministered peptide identified via phage display".
Dai et al. 2007. *Protein Engineering, Design & Selection*. 20(2):69-79. "The Creation of a novel fluorescent protein by guided consensus engineering".
Duerr et al. 2004. *J. Virol. Methods*. 116(2):177-180. "Identification of peptide sequences that induce the transport of phage across the gastrointestinal mucosal barrier".
International Search Report for PCT/US2014/050683 mailed Feb. 2, 2015.
Kim et al. 2007. *J. Controlled Release*. 122(3):375-383. "Transdermal delivery enhanced by magainin pore-forming peptide".
Kumar et al. 2012. *Mol. Pharmaceutics*. 9:1320-1330. "Identification of a Novel Skin Penetration Enhancement Peptide by Phage Display Peptide Library Screening".

(Continued)

Primary Examiner — Jeanette Lieb
(74) Attorney, Agent, or Firm — 3M Innovative Properties Company; Eric E. Silverman

(57) ABSTRACT

Skin penetration enhancers comprising peptides are disclosed. Compositions comprising the skin penetration enhancers are also provided. The compositions further comprise an active agent, such as a pharmaceutically active agent, a vaccine, a cosmetic agent, and a. nutritional supplement. Methods of transdermal ly delivering a pharmaceutically active agent, a vaccine, a cosmetic agent, or a nutritional supplement are also provided.

26 Claims, No Drawings

(56) References Cited

OTHER PUBLICATIONS

Parmley et al. 1988. *Gene.* 73(2):305-318. "Antibody-selectable filamentous fd phage vectors: affinity purification of target genes".

Ravenzwaay. 2004. *Human & Experimental Toxicology.* 23(9):421-430. "A comparison between in vitro rat and human and in vivo rat skin absorption studies".

Scholle et al. 2005. *Combinatorial Chemistry & High Throughput Screening.* 8(6):545-551. "Efficient Construction of a Large Collection of Phage-Displayed Combinatorial Peptide Libraries".

Scott et al. 1990. *Science.* 249(4967):386-390. "Searching for Peptide Ligands with an Epitope Library".

Smirnov et al. 2011. *Vaccine.* 29(33):5434-5442. "Vaccine adjuvant activity of 3M-052: an imidazoquinoline designed for local activity without systemic cytokine induction".

Wan et al. 2009. *Peptides.* 30(2):343-350. "Identification of nose-to-brain homing peptide through phage display".

Wiedersberg et al. 2012. Heather A.E. Benson, Adam C. Watkinson (Eds.), *Transdermal and Topical Drug Delivery: Principles and Practice* (First Edition, Chapter 6, pp. 109-130). John Wiley & Sons, Inc. "Skin Permeation Assessment: Tape Stripping".

PEPTIDES FOR ENHANCING TRANSDERMAL DELIVERY

CROSS REFERENCE TO RELATED APPLICATIONS

This application is a national stage filing under 35 U.S.C. 371 of PCT/US2014/050683, filed Aug. 12, 2014, which claims the benefit of U.S. Provisional Application No. 61/864,964, filed Aug. 12, 2013, the disclosures of which are incorporated by reference in their entirety herein.

This application has associated with it a sequence listing with the file name Sequence_Listing_74320US002.TXT, created Aug. 11, 2014. The sequence listing file contains 4,556 bytes and it is incorporated herein by reference in its entirety.

BACKGROUND

Skin provides an ideal delivery location for many drugs, including systemic drugs. Drug delivery through skin can be painless and provide sustained release, thereby increasing patient compliance. Systemic drugs delivered through skin do not undergo first pass metabolism, and skin delivery can allow systemic treatment with drugs, such as protein-based pharmaceuticals like antibodies and vaccines, that are otherwise susceptible to degradation or digestion in the gastrointestinal tract.

In addition, cosmetic ingredients for improving skin health or enhancing the appearance of skin must also be delivered across the skin's outermost layer, the stratum corneum. However, the delivery of both drugs and cosmetic ingredients across the stratum corneum is complicated by the skin's role as an efficient environmental barrier. The stratum corneum prevents many molecules, such as large molecules, protein drugs, and electrically-charged small molecules, from crossing its barrier.

Various methods have been explored for transporting drugs and cosmetics through the stratum corneum, including physical and chemical disruption of the stratum corneum. While chemical penetration enhancers have been used with varying success, they generally cannot transport large hydrophilic compounds, protein drugs, or electrically-charged small molecules across the stratum corneum and into systemic circulation. Instead, large hydrophilic compounds, protein drugs, and electrically-charged small molecules must often be delivered via routes having lower patient compliance, such as injection. Additionally, for molecules that can be transported with the use of chemical penetration enhancers, the chemical penetration enhancers can cause irritation. There remains a need for new penetration enhancing compositions that can provide transport of a wide variety of compounds across the stratum corneum to deeper layers of skin, or into systemic circulation.

SUMMARY

The present disclosure relates generally to skin penetration enhancers comprising peptides for enhancing the transdermal delivery of active agents, such as pharmaceutically active agents, vaccines, cosmetic agents, nutritional supplements, and the like. The skin penetration enhancers described herein can be used to improve the penetration of various compounds, including small drugs with electric charges and large protein drugs through the skin.

One aspect of the present disclosure provides a skin penetration enhancer comprising a peptide. The peptide can comprise an amino acid sequence comprising ten consecutive amino acid residues as set forth in SEQ ID NO: 1, 2, 3, or 6; eleven consecutive amino acid residues as set forth in SEQ ID NO: 7 or 8; twelve consecutive amino acid residues as set forth in SEQ ID NO: 4 or 5; or analogs thereof. The peptide can comprise 30 or fewer total amino acid residues or amino acid analogs. The peptide can have an amino acid sequence as set forth in SEQ ID NO: 1, 2, 3, 4, 5, 6, 7, 8, 9, 10, 11, 12, 13, 14, 15, 16, or 17.

Another aspect of the present disclosure provides a composition comprising a skin penetration enhancer as disclosed herein and an active agent. The active agent can be selected from the group consisting of a pharmaceutically active agent, a vaccine, a cosmetic agent, and a nutritional supplement; e.g., an antibody, a fat-reduction compound, a therapeutic protein, a hair growth compound, a hair removal compound, or a vitamin.

Another aspect of the present disclosure provides a method of transdermally delivering a pharmaceutically active agent, a vaccine, a cosmetic agent, or a nutritional supplement, the method comprising administering to the skin of a subject in need thereof a composition comprising a carrier selected from a pharmaceutically acceptable carrier, a cosmetically acceptable carrier, or a nutritionally acceptable carrier; an active agent selected from a pharmaceutically active agent, a vaccine, a cosmetic agent, or a nutritional supplement; and a skin penetration enhancer as disclosed herein.

Other features and aspects of the present disclosure will become apparent by consideration of the detailed description.

DETAILED DESCRIPTION

The present disclosure generally relates to penetration enhancers and penetration enhancing compositions comprising peptides. The peptides, penetration enhancers, and compositions provided herein enhance the ability of molecules such as large molecules, protein drugs, and electrically-charged small molecules, to cross the barrier of the stratum corneum, thus avoiding less desirable delivery routes such as injection and increasing patient compliance.

The skin penetration enhancers of the present disclosure reversibly decrease the barrier resistance of the stratum corneum and allow molecules, such as pharmaceuticals, vaccines, nutritional supplements, or cosmetics, to penetrate more readily to the viable tissues, and, in some instances, the systemic circulation. In some instances, the skin penetration enhancer allows molecules such as pharmaceuticals, vaccines, cosmetics, and nutritional supplements to gain entrance to lower levels of the skin, such as the stratum basale and stratum epinosa. In some instances, the skin penetration enhancer allows molecules to gain entrance to the circulatory system or other internal tissues. The terms, "skin penetration enhancer", "penetration enhancer", and "permeation enhancers" are used interchangeably herein.

The skin penetration enhancers described herein allow molecules such as pharmaceuticals, vaccines, cosmetics, and nutritional supplements, including small electrically-charged molecules as well as large molecules such as proteins, to be delivered transdermally. The terms "transdermally" or "transdermal delivery" are generally used to refer to any type of delivery of an active ingredient that crosses any portion of skin. That is, transdermally can generally include systemic delivery (i.e., where the active ingredient is transported across, or substantially through, the dermis such that the active ingredient is delivery into the bloodstream and systemically), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active agent that is transported across at least a portion of the skin (but not necessarily all of the layers of the skin), rather than merely being topically applied to an outer layer of the skin.

Without wishing to be bound by theory, it is believed that the penetration enhancers described herein assist molecules in crossing the stratum corneum by selectively and reversibly modulating the biological processes and signaling pathways that keep the skin a closed barrier to most molecules, thereby allowing transdermal delivery of the desired molecules.

The term "comprises" does not have a limiting meaning where this term appears in the description and claims.

As used herein, "a", "an", "the", "at least one", and "one or more" are used interchangeably.

Also herein, the recitations of numerical ranges by endpoints include all numbers subsumed within that range (e.g. 5 or fewer includes 0.5, 1, 1.25, 2, 2.8, 3, 4, 5, etc.).

As used herein, "analog" refers to a peptide comprising a consecutive amino acid sequence that differs from its parent peptide (e.g., SEQ ID NO: 1-17) by 1-3 amino acid residues, but has the same or similar function of enhancing skin penetration as its parent peptide. In some instances, the differences are conservative amino acid substitutions, in which an amino acid is replaced with another amino acid having a similar side chain or an amino acid analog of similar character. For example, families of amino acids having similar side chains include amino acids with acidic or amide side chains, such as aspartic acid, glutamic acid, asparagines, or glutamine; amino acids with basic side chains, such as lysine, arginine, and histidine; amino acids having uncharged polar side chains, such as glycine, asparagine, glutamine, serine, threonine, tyrosine, and cysteine; amino acids having nonpolar side chains, such as alanine, valine, leucine, isoleucine, proline, phenylalanine, methionine, and tryptophan; amino acids having beta-branched side chains, such as threonine, valine, and isoleucine; and amino acids having aromatic side chains, such as tyrosine, phenylalanine, tryptophan, and histidine. Thus, exemplary conservative amino acid substitutions include substitution of a lysine with a histidine or arginine; substitution of a histidine with a lysine or arginine; substitution of an arginine with a lysine or histidine; substitution of a phenylalanine with a tyrosine or tryptophan; substitution of a tyrosine with a phenylalanine or tryptophan; substitution of a tryptophan with a phenylalanine or tyrosine; substitution of a serine with a threonine; substitution of a threonine with a serine; substitution of an aspartic acid with a glutamic acid; substitution of an asparagine with a glutamine; substitution of a glutamine with an asparagines; substitution of a glycine with an alanine, valine, leucine, isoleucine, or methionine; substitution of an alanine with a glycine, valine, leucine, isoleucine, or methionine; substitution of a valine with a glycine, alanine, leucine, isoleucine, or methionine; substitution of a leucine with a glycine, alanine, valine, isoleucine, or methionine; substitution of an isoleucine with a glycine, alanine, valine, leucine, or methionine; substitution of an aspartic acid with an asparagine or glutamine; substitution of an asparagine with an aspartic acid or glutamic acid; and substitution of a glutamine with an aspartic acid or glutamic acid.

"Analog" also refers to a structural derivative of an amino acid residue that exhibits small differences from the parent amino acid residue. "Analog" further refers to peptides or amino acid residues having small modifications from their parent peptides or amino acid residues known in the art, including but not limited to changing the side chain of one or more amino acid residues or replacing one or more amino acid residues with any non-amino acid.

As used herein, the term "skin" refers to both the outer cutaneous covering of vertebrates, as well as internal mucosal tissue such as oral mucosa, nasal mucosa, esophageal mucosa, etc.

The present disclosure provides skin penetration enhancers comprising a peptide. In one embodiment, the peptide comprises an amino acid sequence comprising ten consecutive amino acid residues, including ACLPGVLGSC (SEQ ID NO: 1), ACSLPWDASC (SEQ ID NO: 2), ACDTPRLTHC (SEQ ID NO: 3), ACLDNTFRAC (SEQ ID NO: 6), or analogs thereof. In one embodiment, the peptide comprises an amino acid sequence comprising eleven consecutive amino acid residues, including ASSTTLNTLAQ (SEQ ID NO: 7), ASSDIPLFTRY (SEQ ID NO: 8), or analogs thereof. In one embodiment, the peptide comprises an amino acid sequence comprising twelve consecutive amino acid residues, including TWTQAWPWGWTW (SEQ ID NO: 4), AKSSWWGRAYWY (SEQ ID NO: 5), or analogs thereof.

In some embodiments, the peptide sequences generally comprise 7-40 amino acid residues. In some embodiments, the peptide sequences generally comprise 10-30 amino acid residues. In some embodiments, the peptide sequences generally comprise 10-20 amino acid residues. In some embodiments, the peptide comprises 30 or fewer total amino acid residues or amino acid analogs. In some embodiments, the peptide comprises 20 or fewer total amino acid residues or amino acid analogs. In some embodiments, the peptide comprises 19 or fewer total amino acid residues or amino acid analogs. In some embodiments, the peptide comprises at least 7 total amino acid residues or amino acid analogs. In some embodiments, the peptide comprises at least 10 total amino acid residues or amino acid analogs. In some embodiments, at least 50% of the amino acid sequence of the peptide comprises a consecutive amino acid sequence selected from SEQ ID NO: 1, 2, 3, 4, 5, 6, 7, or 8, or analogs thereof.

In some embodiments, the skin penetration enhancer comprises a peptide having an amino acid sequence as set forth in SEQ ID NO: 1, 2, 3, 4, 5, 6, 7, 8, or analogs thereof. In some embodiments, the skin penetration enhancer comprises a peptide having an amino acid sequence of SHSACLPGVLGSCGGGS (SEQ ID NO: 9), SHSACSLPWDASCGGGS (SEQ ID NO: 10), SHSACDTPRLTHCGGGS (SEQ ID NO: 11), SHSTWTQAWPWGWTWGGGS (SEQ ID NO: 12), SHSAKSSWWGRAYWYGGGS (SEQ ID NO: 13), SHSACLDNTFRACGGGS (SEQ ID NO: 14), SHSASSTTLNTLAQWPA (SEQ ID NO: 15), SHSASSDIPLFTRYGGGS (SEQ ID NO: 16), SHSACLDNTFRACG (SEQ ID NO: 17) or analogs thereof. In some embodiments, the N-terminus of the peptide comprises a consecutive amino acid sequence of SHS. In some embodiments, the C-terminus of the peptide comprises a consecutive amino acid sequence selected from the group consisting of GGGS, G, and WPA. The present disclosure also provides isolated peptides having an amino acid sequence as set forth in SEQ ID NO: 1, 2, 3, 4, 5, 6, 7, 8, 9, 10, 11, 12, 13, 14, 15, 16, 17, or analogs thereof.

The peptides of the present disclosure may be synthesized using known techniques, such as by Solid-Phase Peptide Synthesis (SPPS). In some embodiments, the peptides of the present disclosure may be partially or completely isolated or purified through known techniques, such as cell tissue, or organ fractionation, chromatographic or electrophoretic techniques.

The present disclosure also provides skin penetration enhancers comprising fusion or chimeric peptides. The fusion or chimeric peptides comprise a first peptide and a second peptide or protein. In some embodiments, the first peptide is a peptide comprising an amino acid sequence comprising SEQ ID NO: 1-8, or analogs thereof. In some embodiments, the first peptide is a peptide has an amino acid sequence as set forth in SEQ ID NO: 1-17, or analogs thereof. The second peptide or protein is different from the first peptide, e.g., has an amino acid sequence not substantially identical to the first peptide. The first peptide and the second peptide or protein are operatively linked, e.g., fused, such that the fusion or chimeric peptide possesses the activity of both the first peptide and the second peptide or protein.

In some embodiments, the skin penetration enhancers are conjugated to an active agent, such as a pharmaceutically active agent, a vaccine, a cosmetic agent, or a nutritional supplement, to form a conjugate. Conjugation is specifically distinguished from simple mixtures of the skin penetration enhancer and active agent. Unlike simple mixtures, the conjugates maintain a chemical or physical association after application to the skin. The conjugates possess the activity of both the skin penetration enhancer peptide and the active agent. Conjugates may be formed using known techniques, such as covalent bonding non-covalent affinity binding, ionic binding, hydrophilic or hydrophobic affinity, physical entrapment, and the like.

In some embodiments, the skin penetration enhancers provided herein can be applied directly to skin or mucosal tissue prior to application of an active agent or composition comprising an active agent. The skin penetration enhancers provided herein can be applied directly to skin or mucosal tissue prior to application of a transdermal delivery device, such as a transdermal patch.

In another embodiment, the present disclosure also provides compositions for enhancing the transdermal delivery of various active agents. The compositions comprise the peptide penetration enhancers herein disclosed and an active agent. In some embodiments, the active agent is a pharmaceutically active agent, a vaccine, a cosmetic agent, or a nutritional supplement.

In one embodiment, the skin penetration enhancers and compositions provided herein can be provided as topical or transdermal formulations, such as a cream, a gel, a foam, a spray, an ointment, a lotion, a solution, a suspension, an aerosol formulation, a non-aerosol spray, an emulsion, a microemulsion, a dispersion, a paste, a powder, a solid stick (e.g., wax- or petroleum-based sticks), a wipe, an oil, or the like.

In another embodiment, the skin penetration enhancers and compositions provided herein may be included in transdermal drug delivery devices, such as a tape, an adhesive transdermal patch, a sheet, a dressing or any other form known to those skilled in the art. In some embodiments, the device will be in the form of a drug reservoir, such as a patch of a size suitable to deliver a selected amount of active agent through the skin.

Any transdermal patch suitable for the continuous transdermal delivery of a therapeutically effective amount of an appropriate active agent may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing PSA reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In some embodiments, the skin penetration enhancers and compositions provided herein are included in a reservoir having an impermeable backing that substantially or fully inhibits migration of drug and/or excipients from the reservoir into the skin-contact adhesive of the dressing. Selection of an appropriate impermeable backing will depend upon the composition of the reservoir and one skilled in the art may readily determine a suitable backing by testing dressings for active agent and/or excipient migration. Typical impermeable barriers include films containing one or more polyethylene terephthalate layers and/or an aluminum barrier layer. In one embodiment, the impermeable backing can function to limit oxygen and/or water vapor permeation. Examples of impermeable backings include films having plasma-deposited amorphous glass layers, such as described in WO 2011/066493 (Kluge et al. to 3M), and films having translucent inorganic barrier layers, such as described in U.S. Patent Application Publication No. 2004/202708 (Roehrig et al. to 3M).

In another embodiment, the skin penetration enhancers and compositions provided herein are included in a drug reservoir in the form of a matrix layer containing the active agent, the matrix layer being adhered to the skin-contact adhesive of the dressing. Such a matrix may be an adhesive layer, as described above. Alternatively the matrix layer may be non-adhesive or weakly adhesive and rely upon the surrounding rim of skin-contact adhesive on the adhesive dressing to secure the patch in place and keep the drug reservoir in contact with the skin surface.

In another embodiment, the skin penetration enhancers and compositions provided herein are included in a drug reservoir in the form of solid particles embedded on the surface or within the skin-contact adhesive of the adhesive dressing. In particular, these particles may be hydrophilic, so that contact with aqueous fluid exposed at the surface of the treated skin will cause them to dissolve or disintegrate, thus releasing active agent into the skin.

In another embodiment, the skin penetration enhancers and compositions provided herein are included in a drug reservoir within the skin-contact adhesive of the adhesive dressing. The active agent may be mixed with the skin-contact adhesive prior to forming the adhesive dressing or it may be applied to the skin-contact adhesive of the adhesive dressing in a separate process step. Examples of suitable methods for applying an active agent to an adhesive layer may be found in U.S. Patent Application Publication No. 2003/054025 (Cantor et al.) and U.S. Pat. No. 5,688,523 (Garbe et al.), the disclosures of which are hereby incorporated by reference.

Release liners are available from a variety of manufacturers in a wide variety of proprietary formulations. Those skilled in the art will normally test those liners in simulated use conditions against an adhesive of choice to arrive at a product with the desired release characteristics. The materials used to supply the liners for the dressings of the present disclosure can be substantially more rigid than the backing Liners which can be suitable for use in the adhesive composites of the present disclosure can be made of kraft papers, polyethylene, polypropylene, polyester or composites of any of these materials. The liners can be coated with release agents such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

The compositions provided herein comprise one or more active agents. As used herein, "active agent" refers broadly to any agent providing any treatment, including prophylactic treatment, to a user, whether or not the agent possesses biological activity. Thus, active agents include pharmaceutically active agent, a vaccine, a cosmetic agent, and a nutritional supplement. Additionally, active agents may be active in more than one category of active agent. For example, a pharmaceutically active agent may also operate as a cosmetic agent. Thus, while some agents may be listed herein as only one type of agent (e.g., pharmaceutically active agent), such description is not intended to be limiting. Active agents may include any agent providing any treatment, including proteins or electrically-charged small molecules.

In one embodiment, active agents may include pharmaceutically active agents, such as antimicrobial agents, antibiotics; antimycotic agents; antibacterial agents; antifungal agents; antiviral agents; anti-phlogistics; anti-pruritic agents; anti-psoriatic agents; antitussive agents; anti-alopecia agents; anti-acne agents; anti-inflammatory agents; local anesthetics; immune response modifying agents, pain relieving agents, growth factors, hormones, therapeutic proteins, and the like.

Exemplary pharmaceutically active agents to be delivered transdermally with the aid of the skin penetration enhancers described herein are capable of local or systemic effect when administered to the skin. Some examples include clonidine, estradiol, nicotine, nitroglycerine, scopolamine, and fentanyl, which are commercially available in the form of transdermal devices. Other examples include anti-inflammatory compounds, both steroidal (e.g., hydrocortisone, prednisolone, triamcinolone) and nonsteroidal (e.g., naproxen, piroxicam, diclofenac); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., IC1204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-l-yl)butyl]methanesulfonamide, and acyclovir); local anesthetics (e.g., benzocaine, propofol, lidocaine, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, buprenorphine, fentanyl citrate, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatripan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, pegylated interferon-alpha); and the like, as well as pharmaceutically acceptable salts and esters thereof. The amount of active agent that constitutes a therapeutically effective amount can be readily determined by those skilled in the art with due consideration of the particular drug, the particular carrier, and the desired therapeutic effect.

In one embodiment, active agents that are of a large molecular weight may be delivered transdermally with the aid of the penetration enhancers described herein. Increasing molecular weight of a drug typically causes a decrease in unassisted transdermal delivery. Examples of such large molecules include proteins, peptides, nucleotide sequences, monoclonal antibodies, vaccines, polysaccharides, such as heparin, and antibiotics, such as ceftriaxone.

Vaccines may be therapeutic or prophylactic, and include any material administered to raise either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines (e.g., using dendritic cells), DNA vaccines, recombinant proteins, glycoproteins, and peptides. Examples of suitable vaccines include flu vaccine, including influenza A and B, Lyme disease vaccine, rabies vaccine, measles vaccine, mumps vaccine, chicken pox vaccine, small pox vaccine, hepatitis vaccine, including A, B, and C, pertussis vaccine, rubella vaccine, diphtheria vaccine, encephalitis vaccine, yellow fever vaccine, parainfluenza vaccine, recombinant protein vaccine, DNA vaccines, polio vaccine, therapeutic cancer vaccine, herpes vaccine, including HSV-1 and HSV-2, pneumococcal vaccine, meningococcal vaccine, whooping cough vaccine, tetanus vaccine, typhoid fever vaccine, cholera vaccine, tuberculosis vaccine, vaccines against plague, hemophilus influenza b, adenovirus, BCG, HIV, cytomegalovirus, dengue, feline leukemia, fowl plague, hog cholera, Japanese encephalitis, respiratory syncytial virus, rotavirus, papilloma virus, severe acute respiratory syndrome (SARS), anthrax, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in United States Patent Application Publication No. 2004/0049150 (Dalton et al.), the disclosure of which is hereby incorporated by reference.

See also, e.g., vaccines disclosed in International Publication No. WO 02/24225 (Thomsen et al.).

In another embodiment, small-molecule drugs that are otherwise difficult or impossible to deliver by passive transdermal delivery may be used as active agents. Examples of such molecules include salt forms; ionic molecules, such as bisphosphonates, including sodium alendronate or pamedronate; and molecules with physicochemical properties that are not conducive to passive transdermal delivery.

In some embodiments, exemplary pharmacologically active agent of the invention include: antibacterial agents, such as oxytetracycline, fusidic acid, gentamycine, mupirocin, retapamulin; antimycotic agents, such as nystatin, clotrimazole, miconazole, econazole, ketoconazole, bifonazole, and combinations of imidazole and triazole derivatives, ciclopirox, terbinafine, fluconazole, and amorolfine; antiviral agents, such as aciclovir, valaciclovir, penciclovir, famciclovir, foscarnet (sodium phosphoneformate hexahydrate) and docosanol; anti-inflammatory agents (glucocorticoids), such as hydrocortisone, clobetasone, triamcinolone, betamethasone, mometasone, and clobetasol (and pharmaceutically acceptable salts and derivatives thereof); antiphlogistics/analgesics (NSAID's), such as acetylsalicylic acid, diclofenac, and ibuprofen (and pharmaceutically acceptable salts and derivatives thereof); antipruritic agents, such as glucocorticoids, for example, hydrocortisone, clobetasone, and betamethasone, and local anesthetics, for example, lidocaine and prilocaine (and pharmaceutically acceptable salts and derivatives thereof); antipsoriatic agents, such as calcipotriol and cyclosporine A (and pharmaceutically acceptable salts and derivatives thereof); agents for treatment of eczema and atopic dermatitis: tacrolimus and pimecrolimus (and pharmaceutically acceptable salts and derivatives thereof); antiglaucomateous agents, such as timolol, betaxolol, latanoprost, bimatoprost, and travoprost (and pharmaceutically acceptable salts and derivatives thereof); local anesthetics, such as lidocaine, prilocaine, ropivacaine, mepivacaine, bupivacaine, levobupivacaine, benzocaine, and tetracaine (and pharmaceutically acceptable salts and derivatives thereof); agents for erectile dysfunction, such as alprostadil (prostaglandin El) (and pharmaceutically acceptable salts and derivatives thereof); anti-dandruff agents, such as selenium sulphides, piroctone oleamine and ketoconazole; anti-alopecia agents, such as minoxidil (and pharmaceutically acceptable salts and derivatives thereof); anti-acne agents, such as tretinoin (retinoic acid), adapalene, benzoyl peroxide, clindamycin, azelaic acid (and pharmaceutically acceptable salts and derivatives thereof); wound healing agents, such as fusidic acid (and pharmaceutically acceptable salts and derivatives thereof); insulin; leutinizing hormone releasing hormone; sodium deoxycholate and the like. In some embodiments, the active agent may comprise pharmaceutically acceptable salts or derivatives of the above-mentioned active agents. Examples of pharmaceutically acceptable salts include acidic salts, such as hydrochloride, sulfate, tartrate, maleate, citrate, phosphate, acetate, lactate, and fumarate salts and basic salts such as sodium and potassium salts. See also, e.g., pharmaceutical salts disclosed in S. M. Berge, L. D. Bighley, D. C. Monkhouse, J. Pharm. Sci. 1977, 66, 1-19.

In another embodiment, active agents of the present disclosure may include insulin; interferon-alpha; interferon-beta; calcitonin; gonadotropin-releasing hormone (GnRH); parathyroid hormones such as teriparatide; lidocaine; lidocaine/tetracaine combination; fentanyl; morphine; hydromorphone; oxybutyrin; alprostadil; terbinafine; zolmitriptan; triamcinolone acetonide; as well as pharmaceutically acceptable salts thereof. In one embodiment, the active agent may comprise sodium deoxycholate, as well as pharmaceutically acceptable salts and derivatives thereof.

In some embodiments, active agents of the present disclosure may include cosmetic active agents, such as sunscreens, sunblocking agents, fragrances, perfumes, essential oils, silicones, emollients, humectants, conditioners, moisturizers, antioxidants, steroids or other anti-inflammatory agents, vasodilators, exfoliants such as a-hydroxy acids or β-hydroxy acids, growth factors, enzymes, bleaching or coloring agents, antifungal or antimicrobial agents (including antibiotics and antiseptics such as povidone-iodine, chlorhexidine gluconate, triclosan, p-chloro-m-xyenol, fatty acid monoesters of glycerin and propylene glycol, benzoyl peroxide, hydrogen peroxide, silver and silver salts including, but not limited to, silver chloride, silver oxide and silver sulfadiazine, phenols, miconazole, clotrimazole, ketoconazole, econazole, undecylenic acid and the like), emulsifiers, artificial tanning agents, tanning accelerants, skin soothing agents, skin tightening agents, anti-wrinkle agents, skin repair agents, sebum inhibiting agents, sebum stimulators, protease inhibitors, anti-itch ingredients, agents for inhibiting hair growth, agents for accelerating hair growth, anti-perspirants, antisudoral agents, antidandruff agents, glidants, skin sensates, antiacne treatments, depilating agents, astringents, hair removal compounds, or corn, callus or wart removers, insect repellants such as N,N-diethyl-m-toluamide (DEET), icaridine, and ethyl butyl acetylaminopropionate (and salts and derivatives thereof), powdered or liquid make-ups, fat-reduction compounds, and the like.

In some embodiments, active agents of the present disclosure include dermal fillers. Dermal fillers are compounds or compositions that add volume to cells under the skin and can result in smoothening of skin wrinkles or augmentation of lips. In some embodiments, exemplary dermal fillers can include hyaluronic acid (HA), in particular of sizes ranging between 5,000 and 2,000,000 Daltons; collagen or collagen mimetic; elastin; fibrin; fibronectin; tenascin; vitamin A; polysaccharides such as chitosan and chondroitin, glycosaminoglycans, or proteoglycans; homo copolymers of amino acids such as poly-lysine, polyacrylamide, polyethylene glycol, polylactic acid, and other polymers; melanin and melanin derivatives; natural and synthetic pigments, or combinations thereof. In one embodiment, the dermal filler is covalently or non-covalently bound to a peptide comprising an amino acid sequence comprising SEQ ID NO: 1-8, or analogs thereof. In one embodiment, the dermal filler is covalently or non-covalently bound to a peptide having an amino acid sequence as set forth in SEQ ID NO: 1-17, or analogs thereof. In one embodiment, the dermal filler is present in a mixture with a peptide comprising an amino acid sequence comprising SEQ ID NO: 1-8, a peptide having an amino acid sequence as set forth in SEQ ID NO: 1-17, or analogs thereof.

In one embodiment, the dermal filler comprises a mixture of HA and collagen or collagen mimetics. In one embodiment, the mixture contains HA and collagen (or its mimetics) in a ratio of from about 1:100 to about 100:1. In another embodiment, the ratio between HA and collagen (or its mimetics) is at least about 1:100, at least about 1:50, at least about 1:10, or at least about 1:1.01. In another embodiment, the ratio between HA and collagen (or its mimetics) is not greater than about 100:1, not greater than about 50:1, not greater than about 10:1, or not greater than about 1.01:1. In one embodiment, the dermal filler includes from about 1% to about 99% HA. In one embodiment, the dermal filler includes at least about 1%, 10%, 15%, 20%, 50%, or 95%

HA. In one embodiment, the dermal filler includes no more than 99%, 95%, 50%, 20%, 15%, 10%, or 1% HA. In another embodiment, the dermal filler includes from about 1% to about 99% collagen or collagen mimetics. In one embodiment, the dermal filler includes at least about 1%, 10%, 15%, 20%, 50%, or 95% collagen or collagen mimetics. In one embodiment, the dermal filler includes no more than 99%, 95%, 50%, 20%, 15%, 10%, or 1% collagen or collagen mimetics. Dermal fillers useful in this invention are described in International Publication WO 2013/112488, which is incorporated herein by reference in its entirety.

In some embodiments, active agents of the present disclosure may include nutritional supplements, such as vitamins, herbal extracts, herbal supplements, amino acids, dietary minerals, dietary fiber, and antioxidants.

The compositions provided herein may be formulated with a pharmaceutically, cosmetically, or nutritionally acceptable excipient, carrier, or vehicle. The compositions may further include one or more additives, including colorants, fragrances, flavorings, antiseptics, moisturizers, thickeners, antioxidants, adhesives, suspending agents, dispersing agents, solubilizers, and rheology modifiers.

In some embodiments, particularly where the active agent has an unusually low rate of penetration through skin or mucosal tissue, additional penetration enhancers or permeation enhancers may be included in the formulation. Exemplary additional penetration enhancers include $C_1$-$C_{36}$ fatty acids such as isostearic acid, octanoic acid, and oleic acid; $C_8$-$C_{36}$ fatty alcohols such as oleyl alcohol and lauryl alcohol; lower alkyl esters of $C_8$-$C_{36}$ fatty acids such as ethyl oleate, isopropyl myristate, butyl stearate, and methyl laurate; di(lower) alkyl esters of $C_6$-$C_8$ diacids such as diisopropyl adipate; monoglycerides of $C_8$-$C_{36}$ fatty acids such as glyceryl monolaurate; tetraglycol (tetrahydrofurfuryl alcohol polyethylene glycol ether); tetraethylene glycol (ethanol, 2,2'-(oxybis(ethylenoxy))diglycol); $C_6$-$C_{36}$ alkyl pyrrolidone carboxylates; polyethylene glycol; propylene glycol; 2-(2-ethoxyethoxy)ethanol; diethylene glycol monomethyl ether; N,N-dimethyldodecylamine N-oxide; and combinations of the foregoing. Alkylaryl ethers of polyethylene oxide, polyethylene oxide monomethyl ethers, and polyethylene oxide dimethyl ethers are also suitable, as are solubilizers such as glycerol and N-methylpyrrolidone. The terpenes are another useful class of softeners, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Additional penetration enhancers should minimize skin irritation, skin damage, and systemic toxicity. The compositions of the present disclosure can also contain a counterirritant, for example, methyl salicylate, capsaicin, camphor and menthol.

An amount of the skin penetration enhancers or active agents described herein effective for a given therapeutic, prophylactic, cosmetic, or nutritional application is an amount sufficient to achieve the intended therapeutic, prophylactic, cosmetic, or nutritional application. The precise amount of skin penetration enhancers or active agents used will vary according to factors known in the art including, but not limited to, the physical and chemical nature of the skin penetration enhancers or active agents, the intended dosing regimen, the method of administering the skin penetration enhancers or active agents, and the species to which the formulation is being administered, the type of formulation being administered, and the condition being treated. Accordingly it is not practical to set forth generally the amount that constitutes an amount of skin penetration enhancers or active agents effective for all possible applications. Those of ordinary skill in the art, however, can readily determine the appropriate amount with due consideration of such factors.

The present disclosure also provides methods of transdermally delivering a pharmaceutically active agent, a vaccine, a cosmetic agent, or a nutritional supplement. In one embodiment, the method comprises administering to the skin of a subject in need thereof a composition comprising a carrier selected from a pharmaceutically acceptable carrier, a cosmetically acceptable carrier, or a nutritionally acceptable carrier; an active agent selected from a pharmaceutically active agent, a vaccine, a cosmetic agent, or a nutritional supplement; and a skin penetration enhancer as disclosed herein.

The present disclosure also provides a method of smoothening the skin of a subject in need thereof, comprising contacting the skin with an effective amount of a composition comprising a skin penetration enhancer comprising a peptide as disclosed herein and an active agent comprising a dermal filler disclosed herein. The present disclosure also provides a method of treating wrinkles for a subject in need thereof, comprising contacting the skin with an effective amount of a composition comprising a skin penetration enhancer comprising a peptide as disclosed herein and an active agent comprising a dermal filler disclosed herein. The present disclosure also provides a method for lip augmentation for a subject in need thereof, comprising contacting the skin with an effective amount of a composition comprising a skin penetration enhancer comprising a peptide as disclosed herein and an active agent comprising a dermal filler disclosed herein.

The methods of the present invention may be performed on any suitable subject. Suitable subjects include animals such as humans, non-human primates, rodents, dogs, cats, horses, pigs, sheep, goats, or cows. The compositions of the invention can be applied to skin or mucosal tissue by any suitable method, such as by spraying, dipping, brushing, dropping, rubbing in, or adhering in patch form.

Embodiments

Embodiment 1 is a skin penetration enhancer comprising a peptide, wherein the peptide comprises an amino acid sequence comprising ten consecutive amino acid residues as set forth in SEQ ID NO: 1, 2, 3, or 6; eleven consecutive amino acid residues as set forth in SEQ ID NO: 7 or 8; twelve consecutive amino acid residues as set forth in SEQ ID NO: 4 or 5; or analogs thereof Embodiment 2 is the skin penetration enhancer of embodiment 1, wherein the peptide comprises 30 or fewer total amino acid residues or amino acid analogs.

Embodiment 3 is the skin penetration enhancer of embodiment 1, wherein at least 50% of the amino acid sequence of the peptide comprises a consecutive amino acid sequence selected from SEQ ID NO: 1, 2, 3, 4, 5, 6, 7, or 8.

Embodiment 4 is the skin penetration enhancer of embodiment 1, wherein the peptide has an amino acid sequence as set forth in SEQ ID NO: 1, 2, 3, 4, 5, 6, 7, 8, 9, 10, 11, 12, 13, 14, 15, 16, or 17.

Embodiment 5 is the skin penetration enhancer of embodiment 1, wherein the N-terminus of the peptide comprises a consecutive amino acid sequence of SHS.

Embodiment 6 is the skin penetration enhancer of embodiment 1, wherein the C-terminus of the peptide comprises a consecutive amino acid sequence selected from the group consisting of GGGS, G, and WPA.

Embodiment 7 is the skin penetration enhancer of any one of embodiments 1-6, wherein the peptide has an amino acid sequence as set forth in SEQ ID NO: 10.

Embodiment 8 is the skin penetration enhancer of any one of embodiments 1-6, wherein the peptide has an amino acid sequence as set forth in SEQ ID NO: 14.

Embodiment 9 is the skin penetration enhancer of any one of embodiments 1-6, wherein the peptide has an amino acid sequence as set forth in SEQ ID NO: 15.

Embodiment 10 is the skin penetration enhancer of any one of embodiments 1-2 or 5-6, wherein the peptide comprises an analog of the amino acid sequence comprising ten consecutive amino acid residues as set forth in SEQ ID NO: 1, 2, 3, or 6; eleven consecutive amino acid residues as set forth in SEQ ID NO: 7 or 8; or twelve consecutive amino acid residues as set forth in SEQ ID NO: 4 or 5; wherein the analog has no more than three conservative amino acid substitutions.

Embodiment 11 is the skin penetration enhancer of embodiment 10, wherein the analog has no more than two conservative amino acid substitutions.

Embodiment 12 is the skin penetration enhancer of embodiment 10, wherein the analog has no more than one conservative amino acid substitutions.

Embodiment 13 is the skin penetration enhancer of any one of embodiments 1-2 or 5-6, wherein the peptide is an analog of the peptide having an amino acid sequence as set forth in SEQ ID NO: 1, 2, 3, 4, 5, 6, 7, 8, 9, 10, 11, 12, 13, 14, 15, 16, or 17; wherein the analog has no more than three conservative amino acid substitutions.

Embodiment 14 is the skin penetration enhancer of embodiment 13, wherein the analog has no more than two conservative amino acid substitutions.

Embodiment 15 is the skin penetration enhancer of embodiment 13, wherein the analog has no more than one conservative amino acid substitutions.

Embodiment 16 is the skin penetration enhancer of any one of embodiments 13-15, wherein the peptide is an analog of the peptide having an amino acid sequence as set forth in SEQ ID NO: 10.

Embodiment 17 is the skin penetration enhancer of any one of embodiments 13-15, wherein the peptide is an analog of the peptide having an amino acid sequence as set forth in SEQ ID NO: 14.

Embodiment 18 is the skin penetration enhancer of any one of embodiments 13-15, wherein the peptide is an analog of the peptide having an amino acid sequence as set forth in SEQ ID NO: 15.

Embodiment 19 is a composition comprising the skin penetration enhancer of any one of embodiments 1-18 and an active agent, wherein the active agent is selected from the group consisting of a pharmaceutically active agent, a vaccine, a cosmetic agent, and a nutritional supplement.

Embodiment 20 is the composition of embodiment 19, wherein the active agent is an antibody, a fat-reduction compound, a therapeutic protein, an agent for accelerating or stimulating hair growth, a hair removal compound, or a vitamin.

Embodiment 21 is the composition of embodiment 19, wherein the active agent is a pharmaceutically active agent comprising an electrically-charged small molecule or a protein.

Embodiment 22 is the composition of embodiment 21, wherein the pharmaceutically active agent is selected from the group consisting of insulin, leutinizing hormone releasing hormone, or sodium deoxycholate.

Embodiment 23 is the composition of embodiment 19, wherein the active agent is a dermal filler.

Embodiment 24 is the composition of embodiment 23, wherein the dermal filler is selected from the group consisting of hyaluronic acid (HA), collagen, collagen mimetic, elastin, fibrin, fibronectin, tenascin, vitamin A, polysaccharide, amino acid homo copolymer, melanin, melanin derivatives, natural or synthetic pigment, and combinations thereof.

Embodiment 25 is the composition of embodiment 24, wherein the polysaccharide is chitosan, chondroitin, glycosaminoglycan, proteoglycan or combinations thereof.

Embodiment 26 is the composition of embodiment 24, wherein the amino acid homo copolymer is poly-lysine, polyacrylamide, polyethylene glycol, polylactic acid, or combinations thereof.

Embodiment 27 is the composition of embodiment 23, wherein the dermal filler is selected from the group consisting of hyaluronic acid (HA), collagen, collagen mimetic, or combinations thereof.

Embodiment 28 is the composition of any one of embodiments 19-27, comprising a pharmaceutically acceptable excipient, wherein the pharmaceutically acceptable excipient provides a composition in the form of a lotion, a cream, or a patch.

Embodiment 29 is a method of transdermally delivering a pharmaceutically active agent, a vaccine, a cosmetic agent, or a nutritional supplement, the method comprising administering to the skin of a subject in need thereof a composition comprising:

a carrier selected from a pharmaceutically acceptable carrier, a cosmetically acceptable carrier, or a nutritionally acceptable carrier;

an active agent selected from a pharmaceutically active agent, a vaccine, a cosmetic agent, or a nutritional supplement; and the skin penetration enhancer of any one of embodiments 1-18.

Embodiment 30 is a method of smoothening the skin of a subject in need thereof, comprising contacting the skin with an effective amount of a composition of any one of embodiments 19-28.

Embodiment 31 is a method of treating wrinkles for a subject in need thereof, comprising contacting the wrinkles with an effective amount of a composition of anyone of embodiments 19-28.

Embodiment 32 is a method for lip augmentation for a subject in need thereof, comprising contacting the lip with an effective amount of a composition of anyone of embodiments 19-28.

Objects and advantages of this invention are further illustrated by the following examples, but the particular materials and amounts thereof recited in these examples, as well as other conditions and details, should not be construed to unduly limit this invention.

EXAMPLES

Materials

Twenty-nine random M13 phage display peptide libraries, ANL1-ANL29 (described in 'Efficient Construction of a Large Collection of Phage-Displayed Libraries', *Combinatorial Chemistry and High Throughput Screening*, 2005, vol. 8, pp. 545-551) were obtained from Dr. Brian Kay (University of Illinois at Chicago). Five random M13 phage display peptide libraries (Table 1) were obtained from Dr. George P. Smith (University of Missouri-Columbia). Three random M13 phage display peptide libraries, Ph.D.™-12, Ph.D.™-C7C, and Ph.D.™-7, were obtained from New England BioLabs, Inc. (Ipswich, Mass.).

TABLE 1

| Phage Peptide Library Designation | GenBank Accession Number |
| --- | --- |
| F3-6mer | AF246446 |
| F88-15mer | AF246448 |
| F88-Cys2 | AF246451 |
| F88-Cys4 | AF246453 |
| F88-Cys6 | AF246455 |

*E.coli* strain ER 2738 (genotype: F' proA+B+lacIq Δ(lacZ)M15 zzf::Tn10(TetR)/fhuA2 glnV Δ(lac-proAB) thi-1 Δ(hsdS-mcrB)5) was obtained from New England Biolabs (Ipswich, Mass.).

Peptides were chemically synthesized by GenScript USA Inc. (Piscataway, N.J.) using stepwise Solid-Phase Peptide Synthesis (SPPS) methods. The peptides were purified by HPLC to 95% purity and identified by high resolution mass spectrometry.

Luria Bertani (LB) broth powder; Luria Bertani (LB) agar powder; isopropyl-β-D-thiogalactoside (IPTG); 5-bromo-4-chloro-3-indolyl-β-D-galactoside (X-gal); polyethylene glycol-8000; tris-HCl; tetracycline; fluorescein isothiocyanate (FITC) sodium salt; agarose; ovalbumin (product No. A2512), and magnesium chloride were all obtained from Sigma-Aldrich (St. Louis, Mo.).

Green Fluorescent Protein (GFP) was expressed and purified according to the procedure described by Dai, M, et al. in 'The Creation of a Novel Fluorescent Protein by Guided Consensus Engineering', *Protein Engineering, Design & Selection*, 2007, vol. 20 (2), pp. 69-79.

LB Broth Medium: LB broth powder was sequentially reconstituted in one liter of deionized water, autoclaved, and stored at room temperature.

Tetracycline Stock (suspension): Tetracycline was added to ethanol:water (1:1) at a concentration of 20 mg/ml and stored at −20° C. in the dark. The stock suspension was vortexed prior to use.

LB/IPTG/X-gal/tetracycline Petri Plates: A solution containing 15 g of LB agar in 1 L of LB medium was autoclaved and then cooled to <50° C. One milliliter of a solution containing IPTG (1.25 g) and X-gal (1.0 g in DMF (25 mL)) was added to the LB medium followed by the addition of 1 mL of tetracycline stock solution. Aliquots of the solution (15 mL) were poured into Petri plates and the plates were stored at 4° C. in the dark Soft Agar: Tryptone (10 g), yeast extract (5 g), NaCl (5 g), magnesium chloride (1 g), and agarose (7 g) were added to deionized water (1 L). The product was autoclaved, separated into 50 mL aliquots, and stored as a solid at room temperature. Prior to use the soft agar was melted using a microwave oven.

PEG/NaCl Phage Precipitating Solution: Polyethylene glycol-8000 was added at a concentration of 20% (weight/volume) to a 2.5 M solution of NaCl in deionized water. The solution was autoclaved, stored at room temperature.

N-(4- {[4-amino-2-butyl-1H-imidazo[4,5-c]quinolin-1-yl]oxy}butyl)-6-(N'-isopropylidenehydrazino)nicotinamide was prepared according to the synthetic procedure described in PCT Publication No. WO 2012/167081 (Wightman).

ELISA assays were conducted using goat anti-guinea pig IgG-HRP (Santa Cruz Biotechnology, Dallas, Tex.).

Human cadaver skin was stored frozen. Prior to using, the frozen sections were placed in PBS and warmed to room temperature. The phage libraries or synthesized peptide sequences were applied to the stratum corneum side of the skin sample.

Methods

Phage Amplification:

A tube containing LB medium (2 mL) and tetracycline (at a concentration of 20 μg/mL) was inoculated with *E. coli* ER2738 cells and then incubated overnight at 37° C. with shaking (200 rpm). An aliquot (100 microliter) was added to 20 mL of fresh LB medium containing 20 μg/mL of tetracycline. The culture was incubated at 37° C. with shaking (200 rpm) of the flask and the cells were grown to the early-log phase (OD600=0.5). Next, the phage sample was added and the culture was maintained for 4 hours at 37° C. with shaking of the flask.

Phage purification:

*E. coli* ER2738 cells were removed from the phage amplified culture sample by centrifugation at 8000 rpm for 10 minutes. The resulting supernatant solution was added to the PEG/NaCl Phage precipitating solution (at a concentration of one volume of supernatant to five volumes of precipitating solution) and then maintained at 4° C. for 2 hours. The resulting phage precipitate was recovered by centrifuging the sample (8000 rpm for 30 min), removing the supernatant, and re-suspending the phage pellet in 2 mL of Tris-buffered saline (Tris buffered saline reagent prepared as 50 mM Tris-HCl in 150 mM NaCl buffered saline, pH 7.5). The amplified phage product was stored at 4° C.

Phage Titration:

LB Broth Medium (5-10 mL) was inoculated with a single colony of *E. coli* ER2738 and incubated with shaking (200 rpm) at 37° C. until the cells reached the early-log growth phase (OD600=0.5). The culture medium was then dispensed into multiple microfuge tubes (200 microliters per microfuge tube with one tube prepared for each phage dilution). Ten fold serial dilutions of amplified phage product in LB broth medium were prepared and a 10 microliter aliquot from each dilution was added to a separate microfuge tube containing culture medium. Each tube was vortexed and incubated at room temperature for 1-5 minutes.

The contents of each microfuge tube were transferred to a corresponding culture tube containing 3mL of soft agar maintained at 45° C. Each culture tube was then vortexed and the soft agar was poured onto a corresponding prewarmed (37° C.) LB/IPTG/X-gal\tetrayclline Petri plate. The resulting plates were gently tilted and rotated in order to evenly spread the soft agar on the plates. The plates were cooled for five minutes, inverted, and then incubated overnight at 37° C. Plates having approximately 100 plaques were counted providing an adjustment for the dilution factor. Single plaque phages on the plates were selected and further processed for DNA sequencing.

DNA Sequencing of Phages:

*E. coli* ER2738 cell culture (800 microliters of an early-log phase prepared as described above) was added to each well of a 96 deep well plate (each well having a 2 mL volume). Single plaque phages were randomly selected from Petri plates prepared as described in the phage titration procedure. A sterilized toothpick was used to remove a plaque from the Petri plate and transfer it to a well in the 96 well plate. The infected *E. coli* ER2738 cells were incubated for 4 hours at 37° C. with shaking (300 rpm). The liquid cultures were then centrifuged (4000 rpm for 60 min at 4° C.) and an aliquot of the resulting phage supernatant (10 microliters) from each well was sequenced for DNA using the rolling circle amplification method. The DNA sequencing was conducted at MCLAB (South San Francisco, Calif.).

Peptide Selection from Phage Display Libraries:

The selection of peptides that enhance the skin penetration of representative active agent compounds was accomplished using the procedures described in Examples 1 and 2.

Example 1

Phage Display Library Selection for Skin Penetration Enhancement Using a Tape Stripping Procedure Each phage display library (200 microliters in PBS) was applied to a 1 cm$^2$ section of human cadaver skin using a PIPETMAN Classic pipet (Gilson Inc., Middleton, Wis.). Adhesive tape was used to form a square frame that defined the application site. After 1 hour, the application site was washed with PBS to remove phages remaining on the skin surface. Tape stripping of the skin sample was accomplished using Scotch® box tape (3M Company, Maplewood, Minn.). The tape was placed on the skin so that it covered the entire application site, but did not extend beyond the frame border (width of tape strip approximately 1.5 cm). For each application of tape, the tape was secured to the skin with three cycles (3 forward and 3 backward passes) of a 300 g hand held roller. Next the tape was grasped by hand at one end and quickly peeled from the skin surface using a single motion. The exact same procedure of tape stripping was repeated at the phage library application site 23 more times. The tape strips 21-24 were soaked in PBS (5 mL) to recover the phages from the adhesive. In addition the skin sample remaining after the 24$^{th}$ tape stripping procedure was soaked in PBS (5 mL) to recover phages from this sample. The recovered phages were combined and then amplified. The amplified pool of phages was loaded on a new sample of cadaver skin for another round of selection and amplification. A total of four rounds of selection and amplification were completed. After the final (4$^{th}$) selection step, the phages were separated with *E. coli* 2738 on an agar plate according to the procedure for phage titration (described above). The single plaque phages were randomly picked from the agar plate and processed for phage DNA sequencing using the procedure described above. DNA sequences were successfully obtained from 57 of the 96 isolated phage plaques.

Example 2

Phage Display Library Selection for Skin Penetration Enhancement Using an In Vivo Hairless Guinea Pig Procedure Hairless guinea pigs (200 gram females from Charles River Laboratory, Wilmington, Mass.) were anesthetized in a chamber using 3-5% isoflurane in oxygen or air, and maintained at 1.5-3% isoflurane with a co-axial breathing device (COAX-3 obtained from Viking Medical, Medford Lakes, N.J.). Each animal was placed in lateral recumbency on a thermostatically controlled surface with its nose and mouth inside the anesthetic face mask for the duration of the experiment. During the procedure, the animal was monitored for respiration rate and the level of anesthesia was adjusted as required. The section of the back used for loading a phage library was wiped with a 70% isopropanol in water solution.

A phage display library containing about 10$^{11}$ phage particles in 200 microliters of PBS was loaded onto a 1 cm$^2$ section of skin on the back of the animal using a PIPETMAN Classic pipet. In order to both control the humidity and reduce contamination at the application site, a Hill Top Chamber® (Hill Top Research, St. Petersburg, Fla.) was placed over the application site and attached with adhesive. After 1 hour, 10 mL of blood was bled from the heart. The blood was immediately transferred to a vial containing heparin (1000 USP units per mL). The sample of blood (10 mL) was mixed with 50 mL of E. coli ER2738 cells in LB broth medium (early log phase, OD600=0.5) and then added to 300 mL of soft agar. Equal portions of soft agar containing blood and ER2738 (about 7 mL per plate) were added to fifty LB/IPTG/X-gal/tetracycline Petri plates. The plates were incubated overnight at 37° C. The resulting single plaque phages were randomly picked from the agar plate and processed for phage DNA sequencing using the procedure described above. DNA sequences were successfully obtained from 48 of the 96 isolated phage plaques.

Example 3

In Table 2 peptide sequences encoded by the isolated nucleotide sequences of Examples 1 and 2 are displayed (Sequence ID Nos: 1-8). The frequency of each peptide sequence in the recovered plaques is reported.

TABLE 2

| Sequence ID No: | Sequence | Frequency of Sequence in Plaques from Tape Stripping of Human Cadaver Skin Study (n/57) | Frequency of Sequence in Plaques from Hairless Guinea Pig Study (n/48) |
|---|---|---|---|
| 1 | ACLPGVLGSC | 1 | 0 |
| 2 | ACSLPWDASC | 1 | 0 |
| 3 | ACDTPRLTHC | 2 | 0 |
| 4 | TWTQAWPWGWTW | 1 | 0 |
| 5 | AKSSWWGRAYWY | 1 | 0 |
| 6 | ACLDNTFRAC | 2 | 11 |
| 7 | ASSTTLNTLAQ | 9 | 5 |
| 8 | ASSDIPLFTRY | 1 | 4 |

Example 4

Modified versions of peptides Sequence ID Nos: 1-8 (Table 2) were synthesized in which each peptide sequence was flanked with an SHS peptide sequence on the N-terminus and a GGGS (Sequence ID Nos: 9-14 and 16 in Table 3), WPA (Sequence ID No: 15 in Table 3), or G (Sequence ID No: 17) peptide sequence on the C-terminus.

Example 5

An in vitro assay to test for skin penetration enhancement was conducted using hairless guinea pig skin. A full skin sample from the back region of the animal was used. An individual test sample for each peptide in Table 3 was prepared containing the peptide (at a concentration of 1 mg/mL), FITC sodium salt (at a concentration of 10 mg/mL), and PBS (200 microliters). The control sample was prepared containing only FITC sodium salt (at a concentration of 10 mg/mL), and PBS (200 microliters). Each peptide test sample was applied to a separate 1 cm$^2$ section on the stratum corneum side of the guinea pig skin using a PIPETMAN Classic pipet. In the same manner, the control sample was applied. The treated skin samples were covered, maintained at room temperature for 1 hour and then washed with deionized water for 5 minutes to remove any FITC remaining on the skin surface. Tape stripping of each skin application site was accomplished using Scotch® box tape. The tape was placed on the skin so that it covered the entire surface of an individual application site (width of tape strip approximately 1.5 cm). For each tape stripping procedure, the tape was secured to the skin with three cycles (3 forward and 3 backward passes) of a 300 g hand held roller. Next the tape was grasped by hand at one end and quickly peeled from the skin surface using a single motion. The exact same procedure of tape stripping was repeated for a total of 20 tape stripping operations at each application site. The 20th tape strip for each sample was imaged for FITC using ultraviolet light at 340 nm. The presence of a fluorescent spot on the tape indicated penetration of FITC to the 20$^{th}$ tape strip. The results are presented in Table 3.

TABLE 3

| Sequence ID No: | Sequence | Fluorescent Spot Visualized on Tape Strip #20 (Example 5) |
|---|---|---|
| 9 | SHSACLPGVLGSCGGGS | NT |
| 10 | SHSACSLPWDASCGGGS | yes |
| 11 | SHSACDTPRLTHCGGGS | NT |
| 12 | SHSTWTQAWPWGWTWGGGS | yes |
| 13 | SHSAKSSWWGRAYWYGGGS | yes |
| 14 | SHSACLDNTFRACGGGS | yes |
| 15 | SHSASSTTLNTLAQWPA | yes |
| 16 | SHSASSDIPLFTRYGGGS | yes |
|  | Control Sample (No Peptide) | no |

NT = Not Tested

Example 6

An in vitro assay to test for skin penetration enhancement was conducted using human cadaver skin. Two test samples (A and B) and a control sample were prepared. Test sample A contained GFP (at a concentration of 2.55 mg/mL), 0.1 mg of the peptide ACLDNTFRAC (Sequence ID No: 6, Table 2), and PBS (50 microliters). Test sample B contained GFP (at a concentration of 2.55 mg/mL), 0.1 mg of the peptide SHSACLDNTFRACGGGS (Sequence ID No: 14, Table 3), and PBS (50 microliters). The control sample contained GFP (at a concentration of 2.55 mg/mL) and PBS (100 microliters). Each sample was applied to a separate 1 cm$^2$ section of human cadaver skin using a PIPETMAN classic pipet. Adhesive tape was used to form a square frame that defined each application site. The treated skin samples were covered, maintained at room temperature for 2 hours, and then washed with deionized water for 5 minutes to remove any GFP remaining on the skin surface. Tape stripping of each skin application site was accomplished using Scotch® box tape. The tape was placed on the skin so that it covered the entire surface of an individual application site, but did not extend beyond the frame border (width of tape strip approximately 1.5 cm). For each tape stripping procedure, the tape was secured to the skin with three cycles (3 forward and 3 backward passes) of a 300 g hand held roller. Next the tape was grasped by hand at one end and quickly peeled from the skin surface using a single motion. The exact same procedure of tape stripping was repeated for a total of 20 tape stripping operations at each application site. The tape strips were imaged for GFP using ultraviolet light at 340 nm. For test sample A, the deepest penetration of the green fluorescent signal of GFP in the skin sample was to tape strip 14. For test sample B, the deepest penetration of the green fluorescent signal of GFP in the skin sample was to tape strip 20. For the control sample, the deepest penetration of the green fluorescent signal of GFP in the skin sample was only to tape strip 6.

Example 7

An in vitro assay to test for skin penetration enhancement was conducted using hairless guinea pig skin. A full skin sample from the back region of the animal was used. The test sample was prepared containing FITC sodium salt (at a concentration of 0.05 mg/mL), the peptide SHSACLDNTFRACG (Sequence ID No: 17) at a concentration of 2.5 mg/mL, and PBS (40 microliters). The control sample was prepared containing only FITC sodium salt (at a concentration of 0.05 mg/mL), and PBS (40 microliters). Each sample was applied to a separate 0.25 cm$^2$ section on the stratum corneum side of the guinea pig skin using a PIPETMAN Classic pipet. The treated skin samples were covered, maintained at room temperature for 3 hours and then at 4° C. overnight. The side of the skin sample opposite the application side was visually examined under ultraviolet light (340 nm). Visualization of a fluorescent spot on the side of the skin directly opposite from the application site was used to confirm penetration of FITC through the skin. For the test sample a fluorescent spot was visualized on the side of the skin directly opposite from the application site. For the control sample a fluorescent spot was not visualized on the side of the skin directly opposite from the application site.

Example 8

An in vivo topical vaccination study was coducted using SHSACLDNTFRACGGGS (Sequence ID No: 14) as the skin penetration enhancer. The ovalbumin antigen was covalently bonded to a Toll-like receptor (TLR) based vaccine adjuvant component following the general procedure described in PCT Publication No. WO 2012/167081 (Wightman) and incorporated herein by reference. Succinimidyl 4-formylbenzoate (SFB) (Thermo Scientific, Rockford, Ill.) dissolved in dimethyl sulfoxide (DMSO) was added to ovalbumin at a 10 fold molar excess. The solution was then incubated for 2 hours at room temperature. The SFB modified ovalbumin (represented as OVA-SFB) was separated from free SFB by use of a ZEBA spin column (Thermo Scientific) pre-equilibrated with pH 6.0, 0.1 M phosphate buffer containing 0.15 NaCl. This step also changed the pH of the OVA-SFB solution in preparation for the conjugation reaction. Next, the TLR-based vaccine adjuvant component, N-(4-{[4-amino-2-butyl-1H-imidazo[4,5-c]quinolin-1-yl] oxy}butyl)-6-(N'-isopropyidenehydrazino)nicotinamide, was dissolved in DMSO and added to the buffered OVA-SFB in a 5 fold molar excess. The acidic conditions of the reaction medium resulted in deprotection of the acetimine protecting group to form N-(4-{[4-amino-2-butyl-1H-imidazo[4,5-c]quinolin-1-yl]oxy}butyl)-6-hydrazinonicotinamide (represented as TLR-VA) in situ. The resulting product formed by covalent conjugation of OVA-SFB to TLR-VA (represented as OVA-TLRconjugate) was separated from unconjugated components with a ZEBA spin column pre-equilibrated with PBS.

Three vaccine formulations were prepared. Vaccine Formulation 1 contained the OVA-TLRconjugate in PBS at a concentration of 0.625 mg/mL. Vaccine Formulation 2 contained the OVA-TLRconjugate in PBS at a concentration of 2.5 mg/mL. Vaccine Formulation 3 contained the OVA-TLRconjugate (at a concentration of 2.5 mg/mL) and peptide SHSACLDNTFRACGGGS (Sequence ID No: 14, at a concentration of 1 mg/mL) in PBS.

Hairless guinea pigs (200 gram females from Charles River Laboratory) were anesthetized in a chamber using 3-5% isoflurane in oxygen or air, and maintained at 1.5-3% isoflurane with a co-axial breathing device (COAX-3 obtained from Viking Medical). Each animal was placed in lateral recumbency on a thermostatically controlled surface with its nose and mouth inside the anesthetic face mask for the duration of the experiment. During the procedure, the animal was monitored for respiration rate and the level of anesthesia was adjusted as required. The section of the back used as the site for immunization was wiped with a 70% isopropanol in water solution.

Three cohorts of animals were used. In cohort 1 (five animals), each animal was injected subcutaneously with 800 microliters of Vaccine Formulation 1. The total volume of formulation was injected across four injection sites located on the back of the animal (i.e. vaccine formulation 1 was dosed as four separate 200 microliter injections). In cohort 2 (four animals), a total of 800 microliters of Vaccine Formulation 2 was topically applied to each animal. Specifically, the total volume of formulation was administered across four application sites located on the back of the animal. At each of the four sites 200 microliters of Vaccine Formulation 2 was applied to a 1 cm² section of skin using a PIPETMAN Classic pipet. In cohort 3 (five animals), a total of 800 microliters of Vaccine Formulation 3 was topically applied to each animal using the same procedure as described for Vaccine Formulation 2. For all three cohorts, a Hill Top Chamber® was placed over each application site and attached with adhesive. The chambers were removed about 4 to 12 hours post dosing. Cohorts 1 and 2 served as comparative examples.

The animals in each cohort were boosted using the corresponding vaccine formulation and method described above at 3 weeks, 6 weeks, and 9 weeks following the initial immunization. Two weeks following the final boost, the mice were bled. The blood samples were maintained at room temperature for 30 minutes and then centrifuged for 15 minutes at 2000 RCF without active braking The supernatant (serum) from each sample was transferred to a new collection tube and stored at −80° C. The ovalbumin specific antibody titers were determined with serum samples diluted 1/6250 using standard serum ELISA in ovalbumin coated microtiter plates. The specific immune (Ab) responses are reported in Table 4 as the mean OD450 values.

TABLE 4

| Cohort | Animals in Cohort | Immunization Method | Skin Penetration Enhancing Peptide in Formulation | Specific Immune (Ab) Response (mean OD450) | Standard Deviation |
| --- | --- | --- | --- | --- | --- |
| 1 (comparative example) | 5 | Subcutaneous Injection | no | 3.994 | 0.013 |
| 2 (comparative example) | 4 | Topical Application | no | 0.210 | 0.168 |
| 3 (example) | 5 | Topical Application | yes | 2.028 | 0.768 |

The embodiments described above and illustrated in the Examples are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Sequence Listing Free Text

ACLPGVLGSC — SEQ ID NO: 1

ACSLPWDASC — SEQ ID NO: 2

ACDTPRLTHC — SEQ ID NO: 3

TWTQAWPWGWTW — SEQ ID NO: 4

AKSSWWGRAYWY — SEQ ID NO: 5

ACLDNTFRAC — SEQ ID NO: 6

ASSTTLNTLAQ — SEQ ID NO: 7

ASSDIPLFTRY — SEQ ID NO: 8

SHSACLPGVLGSCGGGS — SEQ ID NO: 9

SHSACSLPWDASCGGGS — SEQ ID NO: 10

SHSACDTPRLTHCGGGS — SEQ ID NO: 11

SHSTWTQAWPWGWTWGGGS — SEQ ID NO: 12

SHSAKSSWWGRAYWYGGGS — SEQ ID NO: 13

SHSACLDNTFRCGGGS — SEQ ID NO: 14

SHSASSTTLNTLAQWPA — SEQ ID NO: 15

SHSASSDIPLFTRYGGGS — SEQ ID NO: 16

SHSACLDNTFRACG — SEQ ID NO: 17

What is claimed is:

1. A skin penetration enhancer comprising a peptide, wherein the peptide comprises an amino acid sequence comprising ten consecutive amino acid residues as set forth in SEQ ID NO: 1, 2, 3, or 6; eleven consecutive amino acid residues as set forth in SEQ ID NO: 7 or 8; twelve consecutive amino acid residues as set forth in SEQ ID NO: 4 or 5; or analogs thereof, and further comprising a pharmaceutically acceptable excipient, and wherein the skin penetration enhancer is in a lotion, a cream, or a patch.

2. The skin penetration enhancer of claim 1, wherein the peptide comprises 30 or fewer total amino acid residues or amino acid analogs.

3. The skin penetration enhancer of claim 1, wherein at least 50% of the amino acid sequence of the peptide comprises a consecutive amino acid sequence selected from SEQ ID NO: 1, 2, 3, 4, 5, 6, 7, or 8.

4. The skin penetration enhancer of claim 1, wherein the peptide has an amino acid sequence as set forth in SEQ ID NO: 1, 2, 3, 4, 5, 6, 7, 8, 9, 10, 11, 12, 13, 14, 15, 16, or 17.

5. The skin penetration enhancer of claim 1, wherein the N-terminus of the peptide comprises a consecutive amino acid sequence of SHS.

6. The skin penetration enhancer of claim 1, wherein the C-terminus of the peptide comprises a consecutive amino acid sequence selected from the group consisting of GGGS, G, and WPA.

7. The skin penetration enhancer of claim 1, wherein the peptide has an amino acid sequence as set forth in SEQ ID NO: 10.

8. The skin penetration enhancer of claim 1, wherein the peptide has an amino acid sequence as set forth in SEQ ID NO: 14.

9. The skin penetration enhancer of claim 1, wherein the peptide has an amino acid sequence as set forth in SEQ ID NO: 15.

10. A composition comprising the skin penetration enhancer of claim 1 and an active agent, wherein the active agent is selected from the group consisting of a pharmaceutically active agent, a vaccine, a cosmetic agent, and a nutritional supplement.

11. The composition of claim 10, wherein the active agent is an antibody, a fat-reduction compound, a therapeutic protein, an agent for accelerating or stimulating hair growth, a hair removal compound, or a vitamin.

12. The composition of claim 10, wherein the active agent is a pharmaceutically active agent comprising an electrically-charged small molecule or a protein.

13. The composition of claim 12, wherein the pharmaceutically active agent is selected from the group consisting of insulin, leutinizing hormone releasing hormone, or sodium deoxycholate.

14. The composition of claim 10, wherein the active agent is a dermal filler.

15. The composition of claim 14, wherein the dermal filler is selected from the group consisting of hyaluronic acid (HA), collagen, collagen mimetic, elastin, fibrin, fibronectin, tenascin, vitamin A, polysaccharide, amino acid homo copolymer, melanin, melanin derivatives, natural or synthetic pigment, and combinations thereof.

16. The composition of claim 15, wherein the polysaccharide is chitosan, chondroitin, glycosaminoglycan, proteoglycan or combinations thereof.

17. The composition of claim 15, wherein the amino acid homo copolymer is poly-lysine, polyacrylamide, polyethylene glycol, polylactic acid, or combinations thereof.

18. The composition of claim 10, comprising a pharmaceutically acceptable excipient, wherein the pharmaceutically acceptable excipient provides a composition in the form of a lotion, a cream, or a patch.

19. A method of transdermally delivering a pharmaceutically active agent, a vaccine, a cosmetic agent, or a nutritional supplement, the method comprising administering to the skin of a subject in need thereof a composition comprising:
a carrier selected from a pharmaceutically acceptable carrier, a cosmetically acceptable carrier, or a nutritionally acceptable carrier;
an active agent selected from a pharmaceutically active agent, a vaccine, a cosmetic agent, or a nutritional supplement; and
the skin penetration enhancer of claim 1.

20. A method of smoothening the skin of a subject in need thereof, comprising contacting the skin with an effective amount of a composition of claim 10.

21. A method of treating wrinkles for a subject in need thereof, comprising contacting the wrinkles with an effective amount of a composition of claim 10.

22. A method for lip augmentation for a subject in need thereof, comprising contacting the lip with an effective amount of a composition of claim 10.

23. The method of claim 20, wherein the composition further comprises a pharmaceutically acceptable excipient, wherein the pharmaceutically acceptable excipient provides a composition in the form of a lotion, a cream, or a patch.

24. The method of claim 21, wherein the composition further comprises a pharmaceutically acceptable excipient, wherein the pharmaceutically acceptable excipient provides a composition in the form of a lotion, a cream, or a patch.

25. The method of claim 22, wherein the composition further comprises a pharmaceutically acceptable excipient, wherein the pharmaceutically acceptable excipient provides a composition in the form of a lotion, a cream, or a patch.

26. A skin penetration enhancer comprising a peptide, wherein the peptide comprises an amino acid sequence comprising ten consecutive amino acid residues as set forth in SEQ ID NO: 1, 2, 3, or 6; eleven consecutive amino acid residues as set forth in SEQ ID NO: 7 or 8; twelve consecutive amino acid residues as set forth in SEQ ID NO: 4 or 5; or analogs thereof, with the proviso that when the analog is an analog of any one of SEQ ID NO: 1, 2, 3, 4, 6, 7, or 8, then the analog is a conservative substitution analog.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Phage display library peptides

<400> SEQUENCE: 1

Ala Cys Leu Pro Gly Val Leu Gly Ser Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Phage display library peptides

<400> SEQUENCE: 2

Ala Cys Ser Leu Pro Trp Asp Ala Ser Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Phage display library peptides

<400> SEQUENCE: 3

Ala Cys Asp Thr Pro Arg Leu Thr His Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Phage display library peptides

<400> SEQUENCE: 4

Thr Trp Thr Gln Ala Trp Pro Trp Gly Trp Thr Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Phage display library peptides

<400> SEQUENCE: 5

Ala Lys Ser Ser Trp Trp Gly Arg Ala Tyr Trp Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Phage display library peptides

<400> SEQUENCE: 6

Ala Cys Leu Asp Asn Thr Phe Arg Ala Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Phage display library peptides

<400> SEQUENCE: 7

Ala Ser Ser Thr Thr Leu Asn Thr Leu Ala Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Phage display library peptides

<400> SEQUENCE: 8

Ala Ser Ser Asp Ile Pro Leu Phe Thr Arg Tyr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Phage display library peptides

<400> SEQUENCE: 9

Ser His Ser Ala Cys Leu Pro Gly Val Leu Gly Ser Cys Gly Gly Gly
1               5                   10                  15

Ser

<210> SEQ ID NO 10
<211> LENGTH: 17
<212> TYPE: PRT
<213> ORGANISM: Artificial Sequence
<220> FEATURE:
<223> OTHER INFORMATION: Phage display library peptides

<400> SEQUENCE: 10

Ser His Ser Ala Cys Ser Leu Pro Trp Asp Ala Ser Cys Gly Gly Gly
1               5                   10                  15

Ser

<210> SEQ ID NO 11
<211> LENGTH: 17
<212> TYPE: PRT
<213> ORGANISM: Artificial Sequence
<220> FEATURE:
<223> OTHER INFORMATION: Phage display library peptides

<400> SEQUENCE: 11

Ser His Ser Ala Cys Asp Thr Pro Arg Leu Thr His Cys Gly Gly Gly
1               5                   10                  15

Ser

<210> SEQ ID NO 12
<211> LENGTH: 19
<212> TYPE: PRT
<213> ORGANISM: Artificial Sequence
<220> FEATURE:
<223> OTHER INFORMATION: Phage display library peptides

<400> SEQUENCE: 12

Ser His Ser Thr Trp Thr Gln Ala Trp Pro Trp Gly Trp Thr Trp Gly
1               5                   10                  15

Gly Gly Ser

<210> SEQ ID NO 13
<211> LENGTH: 19
<212> TYPE: PRT
<213> ORGANISM: Artificial Sequence
<220> FEATURE:
<223> OTHER INFORMATION: Phage display library peptides

<400> SEQUENCE: 13

Ser His Ser Ala Lys Ser Ser Trp Trp Gly Arg Ala Tyr Trp Tyr Gly
1               5                   10                  15

Gly Gly Ser

<210> SEQ ID NO 14
<211> LENGTH: 17
<212> TYPE: PRT
<213> ORGANISM: Artificial Sequence
<220> FEATURE:
<223> OTHER INFORMATION: Phage display library peptides

<400> SEQUENCE: 14

Ser His Ser Ala Cys Leu Asp Asn Thr Phe Arg Ala Cys Gly Gly Gly
1               5                   10                  15

Ser

<210> SEQ ID NO 15
<211> LENGTH: 17
<212> TYPE: PRT
<213> ORGANISM: Artificial Sequence
<220> FEATURE:
<223> OTHER INFORMATION: Phage display library peptides

<400> SEQUENCE: 15

Ser His Ser Ala Ser Ser Thr Thr Leu Asn Thr Leu Ala Gln Trp Pro
1               5                   10                  15

Ala

<210> SEQ ID NO 16
<211> LENGTH: 18
<212> TYPE: PRT
<213> ORGANISM: Artificial Sequence
<220> FEATURE:
<223> OTHER INFORMATION: Phage display library peptides

<400> SEQUENCE: 16

Ser His Ser Ala Ser Ser Asp Ile Pro Leu Phe Thr Arg Tyr Gly Gly
1               5                   10                  15

Gly Ser

<210> SEQ ID NO 17
<211> LENGTH: 14
<212> TYPE: PRT
<213> ORGANISM: Artificial Sequence
<220> FEATURE:
<223> OTHER INFORMATION: Phage display library peptides

<400> SEQUENCE: 17

Ser His Ser Ala Cys Leu Asp Asn Thr Phe Arg Ala Cys Gly
1               5                   10